United States Patent [19]

Buysch et al.

[11] Patent Number: 5,712,406
[45] Date of Patent: Jan. 27, 1998

[54] METHOD OF EXTRACTIVE SEPARATION OF DIARYL CARBONATES AND THE ORIGINAL AROMATIC HYDROXY COMPOUNDS FROM REACTION SOLUTIONS

[75] Inventors: Hans-Josef Buysch; Carsten Hesse, both of Krefeld; Johann Rechner, Kempen, all of Germany

[73] Assignee: Bayer Aktiengesellschaft

[21] Appl. No.: 794,435

[22] Filed: Feb. 5, 1997

[51] Int. Cl.⁶ .................................................. C07C 68/08
[52] U.S. Cl. .......................... 558/274; 558/271; 558/272; 558/273
[58] Field of Search ............................ 558/274, 273, 558/272, 271

[56] References Cited

U.S. PATENT DOCUMENTS

| | | | |
|---|---|---|---|
| 5,328,615 | 7/1994 | Pacheco et al. | 210/634 |
| 5,489,703 | 2/1996 | Pacheco et al. | 558/277 |

FOREIGN PATENT DOCUMENTS

| | | |
|---|---|---|
| 450442 | 10/1991 | European Pat. Off. . |
| 507546 | 10/1992 | European Pat. Off. . |
| 583936 | 2/1994 | European Pat. Off. . |
| 583938 | 2/1994 | European Pat. Off. . |
| 27 38 437 | 4/1978 | Germany . |
| 4257546 | 7/1991 | Japan . |

Primary Examiner—Michael G. Ambrose
Attorney, Agent, or Firm—Connolly and Hutz

[57] ABSTRACT

Diaryl carbonate and an aromatic hydroxy compound are simultaneously separated from a crude reaction mixture for producing diaryl carbonates by oxidative carbonylation of the aromatic hydroxy compound and containing the diaryl carbonate and excess hydroxy compound together with the catalyst system, consisting of a noble-metal catalyst, co-catalyst, quaternary salt and a base. The crude reaction mixture is mixed with a covalent aprotic extraction agent, a phase separation is carried out into a donor phase containing the catalyst system and a recipient phase containing the diaryl carbonate and the hydroxy compound in concentrated form, and the diaryl carbonate and the hydroxy compound are isolated from the recipient phase.

7 Claims, No Drawings

METHOD OF EXTRACTIVE SEPARATION OF DIARYL CARBONATES AND THE ORIGINAL AROMATIC HYDROXY COMPOUNDS FROM REACTION SOLUTIONS

The invention relates to extraction of diaryl carbonates and the original aromatic hydroxy compounds from reaction solutions for oxidative carbonylation of aromatic hydroxy compounds. In the reaction, the reaction solution is mixed with a suitable extraction agent, after which the clear recipient phase, enriched with aromatic carbonate and aromatic hydroxy compound, is separated from the donor phase, which contains the catalyst.

It is known to produce organic carbonates, e.g. diphenyl carbonate (DPC), by oxidative reaction of an aromatic hydroxy compound with carbon monoxide in the presence of a noble-metal catalyst (DE-OS 27 38 437). The noble metal is preferably palladium. Additional use can be made of a co-catalyst (e.g. manganese or cobalt salts), a base, a quaternary salt, various quinones or hydroquinones and drying agents. Operation can be in a solvent, preferably methylene chloride. Only a small quantity of organic carbonate is formed in this reaction. No method of separating the carbonate from the complex reaction solution is disclosed.

JP-04 257 546 describes a method wherein organic carbonates are produced by continuously supplying the reactants to a distillation column at 150°–205° C. and 30–50 bar. The water from the reaction is continuously distilled off. One disadvantage of this method is that, in order to remove the water it is necessary to operate in a distillation column which, owing to its construction, permits only short residence times. As a result, the space-time yields obtainable by this method are very low (only 17.8 g/l. h). A reaction in a distillation column necessitates use of large quantities of halides at high temperatures (150°–205° C.). This results in serious corrosion problems, and also in expensive apparatus. It is also known to the skilled man that, under the stated reaction conditions, the preferred co-catalysts (iodides) are unstable and a considerable proportion are oxidised to iodine. This results in heavy losses of the co-catalyst and in formation of by-products, which greatly impairs the selectivity and consequently the economics of this method. At these high temperatures and pressures, furthermore, the homogeneous catalyst system is quickly deactivated, so that this method is not economically usable. In addition, although the water is separated from the reaction, this is not a method of isolating the diaryl carbonate.

EP 450 442 and EP 507 546 describe isolation of DPC by distillation of the reaction solution. Under the stated distillation conditions (about 15 Torr and 100°–200° C.), after distillation for several hours, first phenol and finally colourless DPC are obtained. In EP 507 546 the residue on distillation is treated in air at 700° C. for 16 hours and afterwards consists only of palladium and cobalt. The procedure disclosed here inevitably results in complete loss of the catalyst components tetrabutyl ammonium bromide, benzoquinone and co-acetyl acetonate. In addition to the loss of catalyst components and the resulting side-reactions, the calculated DPC yield is only 6–9%, i.e. only a small proportion of DPC can be isolated by this method. All these disadvantages militate against industrial application, since they make the process expensive and also unselective.

In EP 583 936 and EP 583 938 it is proposed to separate the aromatic carbonate by crystallising the 1:1 adduct of phenol and diphenyl carbonate from the reaction mixture. The disadvantages of this method are the strong cooling required for crystallisation, the slow crystallisation process, the dependence on a high DPC content in the reaction solution, i.e. long reaction times, and the inclusion of catalyst components in the crystals obtained, i.e. separation is incomplete. As a result of the long crystallisation time, large-volume containers are needed for the process, which consequently becomes laborious and cost-intensive. These disadvantages make the process very expensive to apply industrially, and therefore uneconomic.

The object therefore is to discover a gentle method of processing whereby diaryl carbonates can be separated from the catalyst system and from the remaining reaction solution with a high space-time yield and under economic, industrially attainable and reproducible conditions.

It has now surprisingly been found that the said disadvantages can be overcome if the reaction solution is removed from the reactor, intensively mixed with a selective extraction agent, and the phases are then separated into a lower donor phase and an upper recipient phase. The resulting donor phase contains a lower concentration of aromatic carbonate and aromatic hydroxy compound and may contain a small percentage of dissolved recipient together with the catalyst system. Completely unexpectedly, the resulting clear recipient phases consist only of aromatic hydroxy compound, aromatic carbonate and small traces of the catalyst system, in addition to the extraction agent. Another surprising fact is that on conversion to the recipient phase, the aromatic carbonate becomes greatly concentrated compared with the aromatic hydroxy compound.

Accordingly the invention relates to a method of simultaneously separating a diaryl carbonate having the formula

$$R^1-O-CO-O-R^1 \qquad (I)$$

and the original aromatic hydroxy compound having the formula

$$R^1-OH \qquad (II),$$

wherein $R^1$ denotes $C_6$–$C_{12}$ aryl, HO—$C_6H_4$—$C_1$-$C_6$-alkylidene-$C_6H_4$— or $C_6$–$C_{12}$-aryl substituted once or twice in each aryl ring by $C_1$-$C_4$-alkyl, $C_1$-$C_4$-alkoxy or halogen or similarly substituted HO—$C_6H_4$—$C_1$-$C_6$-alkylidene-$C_6H_4$, from crude reaction mixtures for oxidatively reacting the aromatic hydroxy compound (II) with carbon monoxide in the presence of a catalyst system containing noble metal, characterised in that the crude reaction mixture is mixed with a proportion by weight of 0.1–20 parts, preferably 0.2–10 parts, particularly preferably 0.3–5 parts, per part of reaction mixture, with a covalent aprotic extraction agent at 20°–150° C., preferably 30°–120° C., particularly preferably 40°–100° C. and 1–200 bar, preferably 1–100 bar, particularly preferably 1–50 bar whereafter spontaneous phase separation into a lower donor phase and an upper recipient phase is brought about at 20°–150° C. and the diaryl carbonate (I) and the aromatic hydroxy compound are isolated from the recipient phase.

In the method according to the invention, mixing and also phase separation of course depend on the size and composition of the reacting batch. The lower limit is 0.05 h and the upper limit does not exceed 30 h, preferably 10 h.

The crude reaction mixture for treatment according to the invention contains 0.1–3 wt. %, preferably 1–2 wt. % of quaternary salt, 0.1–2 wt. %, preferably 0.5–1.5 wt. % water, 5–500 ppm, preferably 20–250 ppm Pd, 10–1000 ppm, preferably 250–750 ppm co-catalyst, 0.01–1 wt. %, preferably 0.1–0.5 wt. % base and 95–98.5 wt. % of aromatic hydroxy compound together with diaryl carbonate.

Phase separation occurs spontaneously, but may also be assisted by centrifuging.

The resulting loaded recipient solutions can be additionally processed without difficulty, e.g. by distillation and/or crystallisation, since they no longer contain any interfering concentrations of catalyst.

The proportion of separated diaryl carbonate can be 2 to 100%, preferably 5 to 90, particularly 5 to 80% of the diaryl carbonate in the crude product. The ratio of diaryl carbonate to aromatic hydroxy compound in the loaded recipient is between 0.001 and 30, preferably 0.01 and 15.

The method according to the invention is suitable for partial or complete separation of diaryl carbonate crude product from oxidative carbonylation of aromatic hydroxy compounds, e.g. of phenol to diphenyl carbonate. Depending on the reaction conditions, processing time and concentration of catalyst, the diaryl carbonate content of the crude solution can be from 5 to 95 wt. % and the concentration of aromatic hydroxy compound can be between 95 and 5 wt. %, relative to the total mount of diaryl carbonate and aromatic hydroxy compound.

A dilute reaction solution can also be concentrated to the desired diaryl carbonate content by gentle distillation. In another embodiment, the desired DPC content can be adjusted before extraction by adding DPC to the reaction solution.

The gas phase superposed during the entire extraction process can be stationary or constantly renewed and can consist of a reaction gas, an inert gas, or a mixture of the two. The inert gas in the method according to the invention can be nitrogen, hydrogen, carbon dioxide, noble gases or organic compounds which are stable and do not cause disturbance under the extraction conditions. In simple and therefore advantageous manner, the method according to the invention is carried out under CO or CO/$O_2$ reaction gas or CO/$O_2$/inert gas.

The extraction process according to the invention can be applied to reaction solutions for oxidative carbonylation of aromatic hydroxy compounds, e.g. phenol, o-, m- or p-cresol, o-, m- or p-chlorophenol, o-, m- or p-ethyl phenol, o-, m- or p-propyl phenol, o-, m- or p-methoxyphenol, 2,6-dimethyl phenol, 2,4-dimethyl phenol, 3,4-dimethyl phenol, 1-naphthol, 2-naphthol and bisphenol A, preferably phenol, the corresponding diaryl carbonate being present. In the case of substitution of the aromatic hydroxy compound there are generally one or two substituents in the form of $C_1$–$C_4$-alkyl, $C_1$–$C_4$-alkoxy or halogen, such as fluorine, chlorine or bromine. $C_6$–$C_{12}$-aryl is generally phenyl, naphthyl or diphenyl. The group HO—$C_6H_4$—$C_1$-$C_6$-alkylidene-$C_6$—$H_4$ is the radical of a bisphenol obtainable by condensation of two molecules of a phenol, optionally substituted to the stated extent, with an oxo compound. The following are examples of oxo compounds with 1–6 carbon atoms for this purpose: formaldehyde, acetaldehyde and other aliphatic aldehydes up to caproic aldehyde, or acetone, methyl ethyl ketone, diethyl ketone and aliphatic $C_5$ or $C_6$ ketones with a homologous structure, or cyclopentanone and cyclohexanone.

Preferred diaryl carbonates and original aromatic hydroxy compounds generally have the formulae:

(III)

and

(IV)

respectively, wherein $R^2$ denotes phenyl, optionally substituted once or twice by $C_1$–$C_4$-alkyl, $C_1$–$C_4$-alkoxy or halogen, preferably unsubstituted phenyl.

The extraction agents can be covalent or aprotic compounds, e.g. halogenated (fluorinated or chlorinated) hydrocarbons with 3–100 carbon atoms, branched or straight-chain alkanes with 3–100 carbon atoms, e.g. propane, butanes, pentanes, hexanes, heptanes, octanes, e.g. n-octane or 2,2,4-trimethylpentane, nonanes, decanes, undecanes, dodecanes, tridecane, tetradecane, pentadecanes, hexadecanes, heptadecanes, octadecanes, nonadecanes, eicosanes, triacontanes, tetracontanes or pentacontanes, branched or unbranched cycloaliphatic compounds with 3–100 carbon atoms, such as cyclobutane, cyclopentane, cyclohexane, cycloheptane, cyclooctane, cyclononane, cycloundecane, cyclododecane, cyclotridecane, methyl cyclopentane, methyl cyclohexane, dimethyl cyclopentane, dimethyl cyclohexane, tetraline and decaline in the form of pure substances, mixtures of these pure substances or fractions from crude-oil distillation such as petroleum ether fractions, ligroin, crude benzine, gas oil or diesel oil, preferably hexane, heptane, octane, nonane, decane or undecane fractions, petroleum ether fractions, ligroin and crude benzine, gas oil, diesel oil, 2,2,4-trimethylpentane and dodecanes, particularly preferably 2,2,4-trimethylpentane and dodecanes. Preferably the halogen hydrocarbons, alkanes and cyclo-aliphatic compounds contain 3–30, particularly preferably 3–20 carbon atoms. All these substances, together with the crude reaction mixture, form a two-phase system consisting of a donor phase and a recipient phase.

In the method according to the invention, diaryl carbonates and aromatic hydroxy compounds can be separated from the crude solutions by methods of extraction such as described e.g. in KIRK-OTHMER, Encyclopedia of Chemical Technology, Fourth Edition, Volume 10, 1993, pages 125–181 and in Ullmann's Encyclopedia of Industrial Chemistry, Fifth Edition, Volume B3, Unit Operations II, 1988, Chapter 6, Liquid-Liquid Extraction, pages 6-1 to 6-61. For example, extraction apparatus in the following classification groups can be used: columns without energy input, columns with pulsed liquid or pulsed components, columns with rotating components, mixer-settlers or centrifugal extractors. The following are examples of columns without energy input: spray columns, packed columns and perforated-tray columns, which differ in the dispersion of the phases. Examples of columns with pulsed liquid or pulsed components: pulsed perforated-tray columns, with piston pump, with pulsator after Misek or Wepuko, columns with vibrating perforated trays after Prochazka or Karr. Examples of columns with rotating components: Rotating Disc Contactor (RDC), Asymmetric Rotating Disc Extractor (ARD)), Oldshue-Rushton multiple-mixer column, Kuhni extractor, Scheibel column, SHE extractor and Graesser Contactor. Examples of mixer-settler extractors: Davy McKee mixer settlers, Lurgi tower extractors, IMI, General Mills and Boxtype mixer settlers after Denver. Examples of centrifugal extractors: Podbielniak centrifugal extractor and Robatel centrifugal extractor. The extractors can be operated as individual extractors, parallel extractors or cascades of extractors. When using cascades of extraction apparata, apparatus in one or more classification groups can be operated in a single cascade. The donor and recipient phase can be guided in a cascade in co-current or preferably in counter-current.

The method of extraction according to the invention can be discontinuous or continuous, preferably continuous.

In the method according to the invention the catalyst system, consisting of the noble-metal compound catalyst, the co-catalyst, the quaternary salt and base, remains in the donor phase. This catalyst system continues to be active and can therefore be recycled during the production of diaryl carbonate. Small losses of activity can be made up by partial removal (purging) and appropriate replacement by fresh catalyst system. Otherwise the entire donor phase is recycled for producing diaryl carbonate. The invention therefore also provides a gentle method of separating the entire catalyst system from the diaryl carbonate produced and the excess aromatic hydroxy compound.

The following examples illustrate the method according to the invention without restricting it thereto.

EXAMPLES

The following abbreviations are used:
DPC=diphenyl carbonate, Ph=phenyl, TBAB=tetrabutyl ammonium bromide, AAS=atomic absorption spectrum.

Examples 1–9

50 g reaction solution and 50 g or 25 g extraction agent were successively poured into an apparatus comprising a heated 200-ml surface-ground vessel with agitator, breakwater, condenser and downstream condensation trap, waste-gas connection, thermometer, gassing unit and filling nozzle. The reaction solution had the following composition: 15% DPC, 81.8% PhOH, 1.0% $H_2O$ and 2.2% catalyst system (TBAB, NaOPh, Mn and Pd compound). The DPC:PhOH ratio was 0.18. The solution, brought to 50° C., was intensively mixed for 60 minutes, after which the agitator was switched off. Phase separation began immediately. The lower, black donor phase contained the catalyst system whereas the upper clear solution formed the recipient phase. The solutions were investigated separately by gas chromatography. The results are shown in Table 1.

Examples 10–13

50 g reaction solution and 50 g of 2,2,4-trimethylpentane were successively poured into the apparatus in Example 1. The reaction solution had the following composition: 15% DPC, 81.8% PhOH, 1.0% $H_2O$ and 2.2% catalyst system (TBAB, NaOPh, Mn and Pd compound). The DPC:phenol ratio was 0.18. The solution, brought to 70° C., was intensively mixed, cooled to the desired temperature, and the agitator was switched off. Phase separation began immediately. The bottom, black donor phase contained the catalyst system whereas the top clear solution constituted the recipient phase. The solutions were separately investigated by gas chromatography. The results are shown in Table 2.

Examples 14–16

50 g reaction solution and 50 g of a dodecane isomer mixture were successively poured into the apparatus in Example 1. The reaction solutions had the composition shown in Table 3. The solution, brought to 70° C., was intensively mixed, cooled to the desired temperature and the agitator was switched off. Phase separation began immediately. The bottom, black donor phase contained the catalyst system whereas the top clear solution constituted the recipient phase. The solutions were separately investigated by gas chromatography. The results are shown in Table 3.

Example 17

1000 g reaction solution and 1000 g of 2,2,4-trimethylpentane were successively poured into an apparatus consisting of a heated 3-liter surface-ground vessel with agitator, bottom outlet valve, condenser with downstream condensation trap and waste-gas connection, thermometer, gassing unit and filling nozzle, the bottom, valve being connected to a heated 3-liter separating funnel with a three-way cock and two 2-liter round-bottom flasks with a waste-gas connection. The reaction solution had the following composition: 41.7% DPC, 55.1% PhOH, 1.0% $H_2O$ and 2.2% catalyst system (TBAB, NaOPh, Mn and Pd compound). The DPC:phenol ratio was 0.76. The solution, brought to 70° C., was intensively mixed for 10 minutes, cooled to 50° C. and quickly transferred to the separating funnel (50° C.). Phase separation began immediately. The bottom, black donor phase contained the catalyst system whereas the top clear solution constituted the recipient phase. The solutions were separately collected, each in a 2-liter flask. After extraction the weight of the donor phase was 984.3 g, and the weight of the recipient phase was 1015.7 g. The solutions were freed from the extraction agent by distillation and then analysed by gas chromatography, showing that the recipient phase contained 112.1 g phenol and 103.6 g DPC (DPC:PhOH ratio=0.92), i.e. DPC had concentrated in the recipient. The resulting white extract contained only traces of TBAB. AAS investigations showed only traces of Mn, no Pd and only small quantities of Na. About 25% of the DPC had already been obtained in this single extraction. About 200 g of extraction agent was dissolved in the donor phase.

Example 18

1000 g of a reaction product containing 66.5% DPC (DPC:PhOH ratio about 2.1) was processed as in Example 17. The solutions were freed from the extraction agent by distillation and then analysed by gas chromatography, showing that the recipient phase contained 101.7 g phenol and 256.8 g DPC (DPC:PhOH ratio=2.53) i.e. DPC had concentrated in the recipient. The resulting white extract contained only traces of TBAB. AAS investigations showed only traces of Mn, no Pd and only small quantities of Na. About 38.6% of the DPC had been obtained by this single extraction. About 195 g of extraction agent was dissolved in the donor phase.

Example 19

897.8 g of a reaction product containing 9.7% DPC (DPC:PhOH ratio=about 0.1) as in Example 17 was processed with 897.8 g isooctane. After extraction, the weight of the donor phase was 870.8 g and the weight of the recipient phase was 914.4 g. The solutions were freed from the extraction agent by distillation and then analysed by gas chromatography, showing that the recipient phase contained 107.1 g phenol and 24.8 g DPC (the DPC:PhOH ratio was 0.23), i.e. DPC had concentrated in the recipient. The resulting white extract contained only traces of TBAB. AAS investigations showed only traces of Mn, no Pd and only small quantities of Na. About 28.3% of the DPC was obtained by this single extraction. About 114 g of extraction agent was dissolved in the donor phase.

TABLE 1

| | | Recipient | | | | | Donor | | | | |
|---|---|---|---|---|---|---|---|---|---|---|---|
| Example | Extraction agent | PhOH | TBAB | DPC | Extraction agent | DPC:PhOH ratio | PhOH | TBAB | DPC | Extraction agent | DPC:POH ratio |
| 1 | Petroleum ether | 30.5 | 0.01 | 5.7 | 63.8 | 0.19 | 71.9 | 1.3 | 9.8 | 17.0 | 0.14 |
| 2. | Cyclohexane | 39.3 | 0.8 | 5.7 | 54.2 | 0.15 | 34.8 | 0.6 | 5.0 | 59.6 | 0.14 |
| 3 | n-heptane | 14.9 | 0.02 | 2.5 | 82.6 | 0.17 | 66.2 | 1.4 | 7.2 | 25.2 | 0.11 |
| 4*) | n-heptane | 16.4 | 0.02 | 2.9 | 78.4 | 0.18 | 64.2 | 1.2 | 8.1 | 25.4 | 0.13 |
| 5*) | n-octane | 19.7 | 0.02 | 3.2 | 77.1 | 0.16 | 66.1 | 1.2 | 8.1 | 24.6 | 0.12 |
| 6*) | isooctane | 8.6 | 0.00 | 2.1 | 89.3 | 0.24 | 71.0 | 1.3 | 9.2 | 18.5 | 0.13 |
| 7*) | decanes | 10.5 | 0.02 | 2.1 | 87.4 | 0.20 | 70.3 | 1.4 | 8.0 | 20.3 | 0.11 |
| 8*) | undecane | 11.8 | 0.01 | 2.5 | 85.7 | 0.21 | 70.7 | 1.3 | 9.5 | 18.5 | 0.13 |
| 9*) | dodecane | 12.1 | 0.00 | 2.8 | 85.1 | 0.23 | 70.1 | 1.4 | 9.4 | 19.1 | 0.13 |

*)Experiments with 25 g of extraction agent
Extraction temperature: 50° C.
Amount of extraction agent: 25 or 50 g
Reaction solution (donor): 50 g
Mixing time: 1 h
TBAB was determined as TBA (tributyl amine)
The analyses show the composition of the recipient and the donor phase after phase separation as a GC area percentage

TABLE 2

| | | Recipient | | | | | Donor | | | | |
|---|---|---|---|---|---|---|---|---|---|---|---|
| Example | Extraction temperature | PhOH | TBAB | DPC | Extraction agent | DPC:PhOH ratio | PhOH | TBAB | DPC | Extraction agent | DPC:POH ratio |
| 10 | 30° C. | 4.8 | 0.00 | 1.3 | 93.9 | 0.27 | 74.0 | 1.4 | 9.2 | 15.5 | 0.13 |
| 11 | 50° C. | 8.6 | 0.00 | 2.1 | 89.3 | 0.24 | 71.0 | 1.3 | 9.2 | 18.5 | 0.13 |
| 12 | 60° C. | 9.2 | 0.005 | 1.8 | 88.9 | 0.20 | 68.3 | 1.3 | 8.6 | 21.8 | 0.13 |
| 13 | 70° C. | 26.6 | 0.08 | 3.9 | 69.4 | 0.15 | 67.5 | 1.4 | 6.8 | 24.0 | 0.10 |

Extraction temperature: 30–70° C.
Amount of extraction agent: 50 g
Reaction solution (donor): 50 g
Extraction agent: 2,2,4-trimethylpentane
Mixing time: 0.5 h
TBAB was determined as TBA (tributyl amine)
The analyses show the composition of the recipient and the donor phase after phase separation as a GC area percentage

TABLE 3

| Example | DPC concentration | Educt | | | | | Recipient | | | | | Donor | | | | |
|---|---|---|---|---|---|---|---|---|---|---|---|---|---|---|---|---|
| | | PhOH | TBAB | DPC | Extraction agent | DPC:Ph—OH ratio | PhOH | TBAB | DPC | Extraction agent | DPC:Ph—OH ratio | PhOH | TBAB | DPC | Extraction agent | DPC:POH ratio |
| 14 | 14.0% | 84.8 | 1.2 | 14.0 | 0.0 | 0.16 | 12.0 | 0.0 | 3.3 | 84.7 | 0.28 | 62.8 | 1.4 | 11.3 | 25.0 | 0.18 |
| 15 | 28.6% | 70.2 | 1.2 | 28.6 | 0.0 | 0.41 | 13.4 | 0.0 | 11.2 | 75.4 | 0.83 | 51.2 | 1.4 | 21.4 | 26.6 | 0.42 |
| 16 | 48.9% | 49.9 | 1.2 | 48.9 | 0.0 | 0.98 | 14.3 | 0.0 | 18.7 | 67.0 | 1.30 | 37.5 | 1.4 | 35.3 | 26.5 | 0.94 |

Extraction temperature: 30–70° C.
Amount of extraction agent: 50 g
Reaction solution (donor): 50 g
Extraction agent: dodecanes
Mixing time: 0.5 h
TBAB was determined as TBA (tributyl amine)
The analyses show the composition of the recipient and the donor phase after phase separation as a GC area percentage.

We claim:

1. A method of simultaneously separating a diaryl carbonate having the formula $$R^1-O-CO-O-R^1 \qquad (I)$$

and the original aromatic hydroxy compound having the formula $$R^1-OH \qquad (II),$$

wherein $R^1$ denotes $C_6$–$C_{12}$ aryl, HO—$C_6H_4$—$C_1$–$C_6$-alkylidene-$C_6H_4$— or $C_6$–$C_{12}$-aryl substituted once or twice in each aryl ring by $C_1$–$C_4$-alkyl, $C_1$–$C_4$-alkoxy or halogen or similarly substituted HO—$C_6H_4$—$C_1$–$C_6$-alkylidene-$C_6H_4$, from crude reaction mixtures for oxidatively reacting the aromatic hydroxy compound (II) with carbon monoxide in the presence of a catalyst system containing noble metal, comprising the steps of (1) mixing the crude reaction mixture with a proportion by weight of 0.1–20 parts, per part of reaction mixture, with a covalent aprotic extraction agent at 20°–150° C. and 1–200 bar, whereafter spontaneous phase separation into a lower donor phase and an upper recipient phase is brought about at 20°–150° C. and (2) isolating the diaryl carbonate (I) and the aromatic hydroxy compound from the recipient phase.

2. A method according to claim 1, wherein the diaryl carbonate and the aromatic hydroxy compound have the formulae $R^2$—O—CO—O—$R^2$ (III) and $R^2$—OH (IV) respectively, and $R^2$ denotes phenyl, optionally substituted once or twice by $C_1$–$C_4$-alkyl, $C_1$–$C_4$-alkoxy or halogen.

3. A method according to claim 2, wherein $R^2$ is phenyl.

4. A method according to claim 1, wherein the extraction agent is selected from the group consisting of halogenated hydrocarbons, alkanes and cycloaliphatic compounds containing 3–100 carbon atoms.

5. The method of claim 1 wherein the crude reaction mixture contains 0.1–3 wt. % quarternary salt, 0.1–2 wt. % water, 5–500 ppm Pd, 10–10,000 ppm co-catalyst, 0.01–1 wt. % base, and 95–98.5 wt. % of aromatic hydroxy compound together with diaryl carbonate.

6. The method of claim 1 wherein the diaryl carbonate content of the crude solution can be from 5 to 95 wt. %, and the concentration of aromatic hydroxy compound can be between 95 and 5 wt. %, relative to the total amount of diaryl carbonate and aromatic hydroxy compound.

7. The method of claim 1 wherein the aromatic hydroxy compound is selected from the group consisting of: phenol; o-, m-, or p-cresol; o-, m-, or p-chlorophenol; o-, m-, or p-ethyl phenol; o-, m-, or p-propyl phenol; o-, m-, p-methoxy phenol; 2,6-dimethyl phenol; 2,4-dimethyl phenol; 3,4-dimethyl phenol; 1-naphthol; 2-naphthol; and bisphenol A.

* * * * *